US007842463B2

(12) United States Patent
Kronenberg (10) Patent No.: US 7,842,463 B2
(45) Date of Patent: Nov. 30, 2010

(54) METHOD OF DIAGNOSING EARLY STAGE RENAL IMPAIRMENT (75) Inventor: Florian Kronenberg, Innsbruck (AT)

(73) Assignee: Vitateq Biotechnology Gmbh, Innsbruck (AT)

( * ) Notice: Subject to any disclaimer, the term of this patent is extended or adjusted under 35 U.S.C. 154(b) by 1730 days.

(21) Appl. No.: 10/485,039

(22) PCT Filed: Jul. 23, 2002

(86) PCT No.: PCT/AT02/00219

§ 371 (c)(1),
(2), (4) Date: Jan. 26, 2004

(87) PCT Pub. No.: WO03/010544

PCT Pub. Date: Feb. 6, 2003

(65) Prior Publication Data

US 2004/0234989 A1 Nov. 25, 2004

(30) Foreign Application Priority Data

Jul. 26, 2001 (AT) .............................. A 1167/2001

(51) Int. Cl.
G01N 33/53 (2006.01)
G01N 33/92 (2006.01)

(52) U.S. Cl. ....................... 435/7.1; 435/7.93; 435/7.94; 435/7.95; 436/518; 436/16; 436/71; 436/811; 530/389.3; 530/391.3

(58) Field of Classification Search ...................... 435/6, 435/7.1, 7.93, 7.94, 7.95, 975; 436/518, 436/16, 71, 811; 530/389.3, 391.3
See application file for complete search history.

(56) References Cited

PUBLICATIONS

Lagrost et al., 1989. Evidence for high density lipoproteins as the major apolipoprotein A-IV-containing fraction in normal human serum. Journal of Lipid Research 30: 1525-1534.*
Fu et al., 1996. Translational regulation of human p53 gene expression. EMBO Journal 15: 4392-4401.*
Guo et al., 2002. Induction profile of rat organic anion transporting polypeptide 2 (oatp2) by . . . inducers that activate gene expression through ligand-activated transcription factor pathways. J. Pharmacol. Exp. Therapeutics 300: 206-212.*
Vallejo et al., 2000. Evidence of tissue-specific, post-transcriptional regulation of NRF-2 expression. Biochimie 82: 1129-1133.*
Yokota et al., 1988. Altered expression of the retinoblastoma (RB) gene in small-cell carcinoma of the lung. Oncogene 3: 471-475.*
Aalto-Setälä et al., "Intestinal expression of human apolipoprotein A-IV in transgenic mice fails to influence dietary lipid absorption or feeding behavior," J. Clin. Invest., 93:1776-1786, 1994.
Apfelbaum et al., "Apolipoprotein A-IV synthesis in rat intestine: regulation by dietary triglyceride," Am. J. Physiol., 252:G662-G666, 1987.

Attman and Alaupovic, "Lipid and apolipoprotein profiles of uremic dyslipoproteinemia. Relation to renal function and dialysis," Nephron, 57:401-410, 1991.
Attman et al., "Abnormal lipid and apolipoprotein composition of major lipoprotein density classes in patients with chronic renal failure," Nephrol. Dial. Transplant, 11:63-69, 1996.
Attman et al., "Serum apolipoprotein profile of patients with chronic renal failure," Kidney Int., 32:368-375, 1987.
Bostom and Lathrop, "Hyperhomocysteinemia in end-stage renal disease: prevalence, etiology, and potential relationship to arteriosclerotic outcomes," Kidney Int., 52:10-20, 1997.
Chen and Albers, "Activation of lecithin cholesterol acyltransferase by apolipoproteins E-2, E-3 and A-IV isolated form human plasma," Biochim. Biophys. Acta, 836:279-285, 1985.
Cockcroft and Gault, "Prediction of creatinine clearance from serum creatinine," Nepron, 16:31-41, 1976.
Cohen et al., "Reduced aortic lesions and elevated high density lipoprotein levels in transgenic mice overexpressing mouse apoliopoprotien A-IV," J. Clin. Invest., 99:1906-1916, 1997.
Diallinga-Thie et al., "Tissue sites of degradation of high density lipoprotein apolipoprotein A-IV in rats," Arteriosclerosis, 6:277-284, 1986.
Diepliner et al., "Plasma cholesterol metabolism in end-stage renal disease: difference between treatment by hemodialysis or peritoneal dialysis," J. Clin. Invest., 77:1071-1083, 1986.
Dieplinger et al, "Plasma apolipoprotein A-IV metabolism in patients with chronic renal disease," Eur. J. Clin. Invest., 22(3):166-174, 1992.
Duverger et al., "Characterisation of apoA-IV-containing lipoprotein particles isolated from human plasma and interstitial fluid," Arterioscler. Thromb., 13:126-132, 1993.
Duverger et al., "Protection against atherogenesis in mice mediated by human apolipoprotein A-IV," Science, 273:966-968, 1996.
Dvorin et al., "A determinant for binding and uptake of high density lipoproteins by rat hepatocytes," J. Biol. Chem., 261(33):15714-15718, 1986.
Fujimoto et al., "Increased apolipoprotein A-IV in rat mesenteric lymph after lipid meal acts as a physiological signal for satiation," Am. J. Physiol., 262:G1002-G1006, 1992.
Gaspari et al., "Precision of plasma clearacne of iohexol for estimation of GFR in patients with renal disease," J. Am. Soc. Nephrol., 9:310-313, 1998.
Goldberg et al., "Lipoprotein ApoC-II actiation of lipoprotein lipase. Modulation by apolipoprotein A-IV," J. Biol. Chem., 265:4266-4272, 1990.

(Continued)

Primary Examiner—Mark L Shibuya
Assistant Examiner—James L Grun
(74) Attorney, Agent, or Firm—Fulbright & Jaworski, LLP (57) ABSTRACT There is disclosed a method of diagnosing early stage renal impairment in humans, characterized by the following steps:
  measuring the amount of apoA-IV in a body liquid or tissue sample of a human, and
  comparing the measured amount of apoA-IV with a reference value.

17 Claims, 1 Drawing Sheet

OTHER PUBLICATIONS

Green et al., "Human apolipoprotein A-IV. Intestinal origin and distribution in plasma," *J. Clin. Invest.*, 65:11-919, 1980.

Guyard-Dangremon et al., "Comparative effects of purified apolipoproteins A-I, A-II and A-IV on cholseteryl ester transfer protein activity," *J. Lipid Res.*, 35:982-992, 1994.

Kronenberg et al., "Effect of sample storage on the mesurement of lipoprotein(a), apolipoproteins B and A-IV, total and high-density lipoprotein cholesterol and triglycerides," *J. Lipid Res.*, 35:1318-1328, 1994.

Kronenberg et al., "Lipoprotein(a) serum concentrations and polipoprotein(a) phenotypes in mild and moderate renal failure," *J. Am. Soc. Nephrol.*, 11:105-115, 2000.

Kronenberg et al., "Low apolipoprotein A-IV plasma concentrations in men with coranary artery disease," *J. Am. Coll. Cardiol.*, 36:751-757, 2000.

Kronenberg et al., "Multicentre study of lipoprotein(a) and apolipoprotein(a) phenotypes in patints with end-stage renal disease treated by hemodialysis or continuous amulatory peritoneal dialysis," *J. Am. Soc. Nephrol.*, 6:110-120, 1995.

Kronenberg, "Homocysteine, lipoprotien(a) and fibrinogen: metabolic risk factors for cardiobascular complications of chronic renal disease," *Curr. Opin. Nephrol. Hypertens*, 7:271-278, 1998.

London and Drüeke, "Atherosclerosis and arteriosclerosis in chroninc renal failure," *Kidney Int.*, 51:1678-1695, 1997.

Massey et al., "High serum apolipoprotein AIV levels in renal transplant recipients," *Clin. Nephrol.*, 55(2):156-158, 2001.

Nestel et al., "Increased lipoprotein-remnant formation in chronic renal failure," *New England Journal of Medicine*, 307(6):329-333, 1982.

Rosseneu et al., "Human apolipoprotein A-IV quantitation by sandwich enzyme linked immunosorbent assay," *Clin. Chem.*, 34:739-743, 1988.

Seishima et al., "An increased apo A-IV serum concentration of patints with chronic renl failure on hemodialysis," *Clin. Chim. Acta*, 167:303-311, 1987.

Seishima et al., "Increased serum apoA-IV concentrations in experimental uremic rats," *J. Lipid Res.*, 33:1441-1447, 1992.

Stein et al., "The role of apoliopoprotein A-IV in reverse cholesterol transport studied with cultured cells and liposomes derived from another analog of phosphatidylcholine," *Biochim. Biophys. Acta*, 878:7-13, 1986.

Steinmetz and Utermann, "Activation of lecithin: cholesterol acyltransferase by human apolipoprotein A-IV," *J. Biol. Chem.*, 260:2258-2264, 1985.

Steinmetz et al., "Human apolipoprotein A-IV binds to apolipoprotein A-I/A-II receptor sites promotes cholesterol efflux from adipose cells," *J. Biol. Chem.*, 265:7859-7863, 1990.

Sun et al., "Effects of age, gender, and lifestyle factors on plasma apolipoprotein A-IV concentrations," *Atherosclerosis*, 151:381-388, 2000.

Utermann et al., "Apolipoprotein A-IV: a protein occurring in human mesenteric lymph chylomicrons and free in plasma. Isolation and quandification," *Eur. J. Biochem.*, 99:333-343, 1979.

Verges et al., "Apolipoprotein A-IV levels and phenotype distribution in NIDDM," *Diabetes Care*, 17:810-817, 1994.

Verges et al., "Macrovascular disease is associated with increased plasma apolipoprotien A-IV levels in NIDDM," *Diabetes*, 46:125-132, 1997.

Von Eckardstein et al., "Lipoproteins containing apolipoprotein A-IV but not apolipoprotein A-I take up and esterify cell-derived cholesterol in plasma," *Arterioscler. Thromb. Vasc. Biol.*, 15:1755-1763, 1995.

Wienstock et al., "Decreased HDL cholesterol levels but normal lipid avsorption, growth, and feeding behavior in apolipoprotein A-IV knockout mice," *J. Lipid Res.*, 38:1782-1794, 1997.

Miyata et al., "Serum apolipoprotein A-IV levels increase in diabetic patients with nephropathy," *The Journal of Japan Atherosclerosis Society*, 15(5):1159-1162, 1987.

Attia et al., "Response of apolipoprotein AIV and lipoproteins to glycaemic control in young people with insulin-dependent diabetes mellitus," *Diabet Med.*, 14(3):242-247, 1997. Abstract Only.

Black and Ellinas, "Apolipoprotein synthesis in newborn piglet intestinal explants," *Pediatr. Res.*, 32(5):553-558, 1992. Abstract Only.

Coresh et al., "Calibration and random variation of the serum creatinine assay as critical elements of using equations to estimate glomerular filtration rate," *Am J Kidney Dis.*, 39(5):920-929, 2002.

Elshourbagy et al., "Expression of rat apolipoprotein A-IV and A-I genes: mRNA induction during development and in response to glucocorticoids and insulin," *Proc Natl Acad Sci U S A*, 82:8242-8246, 1985.

Kronenberg et al., "Apolipoprotein A-IV serum concentrations are elevated in patients with mild and moderate renal failure," *J. Am. Soc. Nephrol.*, 13:461-469, 2002.

Levey et al., "Definition and classification of chronic kidney disease: a position statement from Kidney Disease: Improving Global Outcomes (KDIGO)," *Kidney Int.*, 67(6):2089-100, 2005.

Tso et al., "Gastrointestinal satiety signals IV. Apolipoprotein A-IV," *Am J Physiol Gastrointest Liver Physiol.*, 286(6):G885-G890, 2004.

* cited by examiner

FIG. 1

METHOD OF DIAGNOSING EARLY STAGE RENAL IMPAIRMENT

This application is a national phase application under 35 U.S.C. §371 of PCT Application No. PCT/AT02/00219 filed 23 Jul. 2002, which claims priority to Austrian Application No. A 1167/2001 filed 26 Jul. 2001, the contents of which are incorporated herein by reference in their entirety.

The invention relates to a method of diagnosing early stage renal impairment.

Glycoprotein apolipoprotein A-IV (apoA-IV) is almost exclusively produced in intestinal human enterocytes and secreted into the lymph (1). It is a structural protein of chylomicrons, and the mean plasma levels are approximately 15 mg/dl (2). In the fasting state, the majority of apoA-IV circulates in plasma as part of a lipid-poor, small HDL-like particle that does not contain apoA-I (3, 4). The physiologic function of apoA-I is not yet clear and controversial, respectively. It was postulated to be involved in fat absorption (5) and regulation of food intake (6), yet none of these findings could be confirmed in genetically modified mice (7, 8). In vitro studies reported convincing evidence that apoA-IV participates in several steps of the reverse cholesterol transport pathway, which removes cholesterol from peripheral cells and directs it to liver and steroidogenic organs for metabolization (9-11). ApoA-IV activates lecithin-cholesterol acyltransferase (LCAT) (12, 13) and modulates the activation of lipoprotein lipase (14) as well as the CETP-mediated transfer of cholesteryl esters from HDL to LDL (15), suggesting that apoA-IV may represent an antiatherogenic factor. This is supported by studies in both animals and humans. Fat-fed mice that overexpress either human (16) or mouse apoA-IV (17), developed significantly fewer atherosclerotic lesions in the aorta than control mice. This was even observed when apoA-IV was overexpressed in ApoE-deficient mice with high-level atherogenic background (16).

A few studies have investigated apoA-IV in renal patients and observed an increase of apoA-IV. Nestel et al. (18) as well as Seishima and Muto (19) described markedly elevated apoA-IV concentrations in small groups of hemodialysis and CAPD patients. This was confirmed by Dieplinger et al., who observed significant differences in the plasma distribution of apoA-IV with an accumulation of apoA-IV in the high-density lipoproteins (HDL) when compared with controls (20). They suggested that this altered distribution might reflect impaired reverse cholesterol transport in these patients (21). In a large multicenter study on 534 hemodialysis and 168 CAPD patients, approximately twofold elevated apoA-IV concentrations were observed (22) compared with controls. As soon as end-stage renal disease has been reached, there seem to be no differences in the apoA-IV concentrations between the two dialysis treatment modalities or between diabetic and non-diabetic patients (22). However, it is not known at which stage of renal impairment apoA-IV starts to rise, and whether it is associated with atherosclerotic complications also in this disease population.

Seishima et al. (Clin. Chim. Acta 167 (1987), 303-311) investigated apoA-IV in patients with terminal renal insufficiency who are treated with hemodialysis, i.e. in a disease of the kidneys in the end stage (kidney substitution therapy).

In Seishima et al. (J. Lipid Res. 33 (1992), 1441-1447), 7 rats. with 5/6 kidney removal were compared with 7 control rats. By this intervention, an experimental kidney function restriction was produced, showing in a marked increase of the BUN (15.2 vs. 56.1 mg/dl) and serum creatinine (0.69 vs. 1.46 mg/dl). apoA-IV was twice as high in the 5/6 nephrectomized rats, with no absolute concentrations but merely an arbitrary unit being indicated.

Yet, it has been known that the rat is a classical HDL animal (and apoA-IV is mainly HDL-associated), and results therefore are not applicable to humans in whom mainly LDL-containing lipoproteins are found.

In Massy et al. (Clin Nephrol. 55 (2001), 156-158) the apoA-IV concentrations in 36 renal transplant patients and 20 control persons were assayed. The creatinine clearance was calculated and not directly measured. Moreover, the patients were under the influence of three potent immune suppressants (Cyclosporin, Azathioprine and corticosteroids) which all have a marked and confirmed influence on the lipoprotein metabolism in humans. Patients who received Cyclosporin moreover had higher apoA-IV levels than those without Cyclosporin. Whether this effect was caused by Cyclosporin itself or by an influence of Cyclosporin on renal function has not been shown.

It has been shown that these two models disclosed in the prior art (that of renal transplantation and that of 5/6 nephrectomized rats) are unsuitable to show an apoA-IV as an early parameter of restricted renal function. For the terminal renal function, this cannot be expected by definition, anyway.

Early diagnoses are always important, particularly in renal diseases. One object of the present invention therefore is to develop a method of diagnosing renal damage in the early stage, i.e. at a time in the course of the renal disease where renal impairment is still slight and the beginning of a therapy promises to be more successful.

This object has been achieved by a method of diagnosing early stage renal impairment in humans, which is characterized by the following steps:

measuring the amount of apoA-IV in a body liquid or tissue sample of a human, and comparing the measured amount of apoA-IV with a reference value.

Suprisingly, in the context of the present invention it could be shown that the rise of the apoA-IV concentration occurs in the very early stages of various renal diseases. As in many other diseases, at a late stage, patients exhibit a plurality of unphysiological levels of proteins (among them, apoA-IV), yet of none of them it has been proven that it is a significant marker in early stage renal impairment. In fact, it has also. been suspected that increased apoA-IV concentrations in patients with renal diseases in the end stage, who receive dialysis, are associated with diabetic complications and processes involved in the dialysis treatment.

It is highly interesting that apoA-IV in the early stages of a renal impairment is increased, whereas other markers of the (fat) metabolism, such as HDL cholesterol, apoA-I or ApoB, have no significant marker function for such an early stage. In fact, the HDL and LDL cholesterol levels were unchanged, whereas the apoA-I and ApoB concentrations in patients were reduced. However, the most significant change in early renal diseases was a rise in the apoA-IV concentrations which in patients was higher by almost 70% than in controls.

Therefore, even a slight. impairment by a renal disease is accompanied by a significant rise in the apoA-IV concentrations, making apoA-IV a relevant and significant marker for a renal impairment in the early stage. Renal impairment in the early stage may be defined by an GFR range of more than 90 ml/min/1.73 m$^2$, e.g. A mean GFR of 120 ml can also be considered as situation of an early stage renal impairment.

Within the scope of the present invention, patients from the earliest to the advanced stages of a restricted renal function were examined. Partially, this restricted function is not at all determinable by conventional measurement methods (the serum creatinine, e.g., in these phases often is still normal, often even the glomerular filtration rate is still normal). This by itself already is proof of the singularity of the study. The renal function was determined by a "gold standard" (Iohexol clearance). The major portion of the references wherein other parameters were measured in these phases of renal insufficiency, mainly used mathematical methods for determining the renal function, which include parameters such as creatinine and age. Yet, it has been sufficiently known that creatinine starts to rise only when the renal function has been restricted by more than 50%. However, in the scope of the present invention, this creatinine-blind range is fully recognized by a clearance procedure. Moreover, according to the examinations carried out according to the invention, the diagnosis of the disease in most of the patients is clearly proven by a biopsy or by ultrasonic means. Thus, according to the invention, a study has been provided for the first time in which the renal function and the basic renal disease have been determined by accepted, valid methods.

The reference value with which the amount of apoA-IV in a sample is compared is preferably obtained from a human who does not have any renal impairment (a healthy human). A renal impairment can then be diagnosed by way of an increased level of the apoA-IV in the body liquid or tissue sample of the human to be examined, e.g. a person who is assumed to suffer from renal impairment.

The method according to the invention is particularly suitable for the routine analysis of healthy humans, i.e. analyses which are carried out annually so as to diagnose renal impairment in a very early stage, i.e. at a time when the probability of healing humans by therapeutic measures usually is a very high one.

An elevated apoA-IV level is seen as a level which is higher than that of a healthy control person. Preferably, this elevated level is higher by at least 20%, preferably by at least 50%, in particular by at least 70%, than the reference level which is taken from a human without a renal impairment. The optimum "healthy" reference value is a reference value obtained from the same human at a healthy stage, i.e. at an earlier time when this human had no renal impairment. Moreover, the relative proof of increased levels will also depend on the method by which the apoA-IV level is measured, i.e. the sensitivity of the relative assay, the reproducibility etc., an important factor for defining the result of the diagnosis.

The comparison between the measured value in the human in whom the diagnosis is to be made with the present invention, and the reference value will also depend on the body fluid or the tissue from which the levels are derived and measured. Preferably, of course, serum will be tested, in which the (healthy) reference value usually will range between 10 and 18 mg of apoA-IV/dl of serum, when tested with apoA-IV ELISA. In such a system, an early stage of a renal impairment can be determined by way of a value higher than 18, preferably higher than 22, in particular higher than 28 mg/apoA-IV/dl serum. As explained above, these absolute values, however, will always depend on the very specific manner of measuring the amount of apoA-IV and on the body fluid or tissue, respectively, in which the apoA-IV amount is measured.

ApoA-IV concentrations which are measured in serum have an extremely high correlation with those values which are measured in plasma. The differences of a few percent can be explained by the common observation that values measured in serum in general are higher by a few percent than those measured in plasma. Thus, it does not make any difference whether the measurements are carried out in plasma or in serum, as long as the results are compared with a reference collective in which the measurements have been carried out in the same "medium".

Preferred sources of material to be tested according to the invention other than blood-derived body fluids can include renal tissue, in particular biopsy material from renal tissue, as well as lymph.

With the method according to the invention, an early stage of any renal impairment can be diagnosed irrespective of the specific pathology of the renal disease prevailing. Preferably, this early stage of a renal impairment is an early stage glomerulonephritis, an early stage polycystic kidney disease, an early stage chronic "pyelonephritis", or an early stage diabetic nephropathy.

Furthermore, it has been analyzed with the present invention that humans suffering from diseases of the coronary arteries or humans with atherosclerotic complications in the early stage of a renal impairment do not have such significantly increased apoA-IV concentrations in comparison to healthy humans. This is also due to the fact that in a human who suffers from such a disease of the coronary arteries or from atherosclerotic complications, apoA-IV is reduced if there is no renal impairment. Therefore, the diagnosis of a renal impairment in the early stage in such humans must be correspondingly adapted to their conditions and should be made by considering the reference levels of humans who suffer from diseases of the coronary arteries or from atherosclerotic complications, yet who do not have any renal impairment (such reference levels for apoA-IV will be lower than in healthy humans). Therefore, if the present method is carried out in humans suffering from diseases of the coronary arteries or from atherosclerotic complications, a reference value should preferably be provided, which indicates the absence of a renal impairment, which is lower than for humans who do not suffer from renal impairment and do not suffer from diseases of the coronary artery or from atherosclerotic complications. In such cases, the lower reference value which indicates the absence of a renal impairment in the early stage, is lower by at least 20%, preferably by at least 40%, in particular by at least 60%, than the reference value for humans who do not suffer from renal impairment and who do not suffer from diseases of the coronary artery or from atherosclerotic complications, either. In this case, the absence of a renal impairment in the early stage may be characterized by a low reference value of from 6 to 14 mg of apoA-IV/dl of serum, as defined above. In such humans who suffer from a disease of the coronary artery or from atherosclerotic complications, an early stage of a renal impairment can be diagnosed by way of a value higher than 14, preferably higher than 18, in particular higher than 22 mg of apoA-IV/dl of serum.

In another aspect, the present invention relates to the use of a method according to any one of claims 1 to 11 for observing the development of renal impairment in an early stage. Therefore, the present invention is also employed for using apoA-IV or apoA-IV-proving or -measuring agents for diagnosing early stage renal impairment.

According to a further aspect, the present invention also relates to a kit for carrying out the inventive method, said kit comprising:
  a vessel containing a sample of a body fluid or a tissue sample from a human suffering from renal impairment or who runs the risk of a renal impairment, or a vessel assumed to be filled with this sample,
  means for measuring the amount of apoA-IV in a body fluid or tissue sample, and
  a reference value means for enabling the diagnosis of an early stage renal impairment in this human.

The means for measuring the amount of apoA-IV can be selected from any suitable means for proving/quantifying apoA-IV, e.g., anti-apoA-IV antibodies, in particular polyclonal antibodies, secondary antibodies, in particular enzymatically or chemically labeled secondary antibodies, apoA-IV-RNA-specific nucleic acids, apoA-IV-specific enzymatic assays, apoA-IV-specific ELISAs or combinations thereof.

The means of the reference level which allows for diagnosing an early stage renal impairment in this human is preferably selected from a vessel with a predetermined amount of apoA-IV, a vessel with a body fluid or tissue sample from a healthy human, a vessel with a body fluid or tissue sample from a human with renal impairment, each preferably in lyophilized form, a calibration curve, instructions for using the kit, or combinations thereof. With the kit, preferably also suitable instructions (e.g. in written form) should be provided, giving specific information as regards the diagnosis of an early stage renal impairment.

In a further aspect, the present invention also relates to a method of diagnosing coronary heart disease in humans who suffer from an (early stage) renal impairment, characterized by the following steps:

measuring the amount of apoA-IV in a body fluid or tissue sample from a human, and comparing the measured amount of apoA-IV with a reference value.

Even though it has been shown that apoA-IV is a relevant marker in the (healthy) normal population, it has been surprising that this protein proved to be a reliable marker for coronary heart disease in humans who suffer from renal diseases, since other markers for coronary heart diseases, such as cholesterol or HDL cholesterol, failed as CHD markers in patients with renal diseases, in particular in dialysis patients. Therefore, it is also possible to analyze coronary heart diseases (or their risk) with the methodology according to the invention.

Often, the evaluation of apoA-IV as predictor for a restricted renal function as well as as a predictor for the presence of an atherosclerosis often is possible only in common. I.e., if a patient has a high apoA-IV, it must be determined whether possibly his renal function is restricted. If the values are low, this may be an indication of a possible atherosclerosis. If apoA-IV is in the "normal range", there may of course be a simultaneous restricted renal function and an atherosclerosis. If, e.g., a patient known to have a restricted renal function has an apoA-IV which is relatively normal for "healthy" persons, it should of necessity be also searched for the presence of atherosclerotic changes.

The present invention will be further characterized by way of the following examples and drawings, yet it is not restricted thereto.

EXAMPLES

Methods

Patients:

In 1997, patients were recruited from eight nephrology departments in Germany (Göttingen, Greifswald, Heidelberg, Homburg/Saar, Munich), Austria (Feldkirch, Innsbruck) and South Tyrol (Bozen), nearly two thirds of the patients coming from two departments (Heidelberg and Innsbruck) (23). White patients aged 19 to 65 years who had visited the outpatient department at least once during the past year were included in this study. Exclusion criteria were serum creatinine >6 mg/dl, diabetes mellitus, malignancy, liver, thyroid or infectious disease at the time of recruitment, nephrotic syndrome, defined as a daily proteinuria >3.5 g/1.73 m$^2$, organ transplantation, allergy to ionic contrast media, and pregnancy. 340 patients fulfilled the criteria, 28 of which could not be reached, and 85 refused to participate in the study. The remaining 227 patients were included in the study, and their characteristics are provided in Table 1. The study was approved by the institutional ethics committees, and the subjects provided written consent.

TABLE 1

Characteristics of patients with renal disease and age- and gender-matched controls[a]

| | Controls (n = 227) | Renal patients (n = 227) |
|---|---|---|
| Age (years) | 45.8 ± 12.3 | 45.7 ± 12.6 |
| Gender, female/male, n | 73/154 | 73/154 |
| Body mass index | 26.4 ± 3.6 | 25.2 ± 3.8[b] |
| GFR, ml/min/1.73 m$^2$ | — | 70 ± 42 [38, 63, 96] |
| Creatinine, mg/dl | 0.99 ± 0.18 | 2.02 ± 1.16[b] |
| Urea, mg/dl | 29 ± 7 | 60 ± 34[b] |
| Proteinuria, g/24 h/1.73 m$^2$ | — | 0.9 ± 0.9 [0.2, 0.6, 1.5] |
| Serum albumin, g/dl | 4.88 ± 0.49 | 4.57 ± 0.41[b] |
| Hematocrit | — | 0.41 ± 0.06 |
| CRP, mg/dl | — | 0.37 ± 0.76 [0.07, 0.16, 0.41] |
| Systol. blood pressure, mm Hg | 129 ± 13 | 137 ± 21[b] |
| Diastol. blood pressure, mm Hg | 81 ± 9 | 87 ± 14[b] |
| Drug-treated hypertension, % | 10.6 | 78.9[b] |
| Smoker/ex-smoker/non-smoker, n | 61/58/108 | 49/57/121 |

[a]Data are mean ± SD and, where applicable, [25$^{th}$ percentile, median, 75$^{th}$ percentile]
[b]P < 0.001 for comparison with controls.

To avoid interobserver differences, all renal patients were recruited by one doctor who visited the participating centers. Patient history, including atherosclerotic events, was recorded by interview and compared with patient records. Each patient underwent a physical check-up. The primary cause of renal disease was glomerulonephritis (GN) in 97 patients (confirmed by biopsy in 90 instances), polycystic kidney disease (PCKD) in 37 patients, chronic "pyelonephritis" (PN) in 24 patients, other types of renal disease in 43 patients, and unknown in 26 patients.

Patients were compared with 227 age- and gender-matched white controls of the same ethnic origin without renal impairment or liver disease who were recruited in 1997 from one of the PROCAM study centers (24).

Laboratory Procedure:

Serum and EDTA plasma were taken after a 12-hour overnight fast. After low-speed centrifugation, samples were frozen and stored at −80° C. before analysis (25). Depending on the serum creatinine level, two to three blood samples were obtained after infusion of iohexol during the same visit in the outpatient department so as to determine the GFR by aid of the iohexol method (26). In 18 patients mostly suffering from advanced impairment of renal function, the GFR was calculated by using the formula of Cockcroft and Gault (27). The patients were carefully instructed regarding the collection of 24-hour urine samples for determining the proteinuria.

The measurements of apoA-IV, Lp(a), serum albumin, GFR, C-reactive protein (CRP) and Apo(a) phenotyping each were effected centrally, or in a single laboratory, respectively, so as to avoid measurement differences between the laboratories. At this time, the laboratory staff cooperating in this study did not know anything about the renal function and medical history of the patients or about the classification of the measured samples into patient or control.

The apoA-IV concentrations in plasma were determined by means of a solid phase enzyme immunoassay which uses the affinity-purified rabbit-anti-human-apoA-IV polyclonal antiserum as the capture antibody and the same antibody coupled to horseradish peroxidase as detection antibody (25, 28). Plasma with a known content of apoA-IV (standardized with purified apoA-IV after the phenyl alanine quantification by high pressure liquid chromatography) served as calibration standard. The intraassay and interassay coefficients of variation of this essay were 4.5% and 6.6%, respectively (25). Samples from patients and controls were analyzed as duplicates within one series in a blinded fashion and after a similar time of sample storage at −70° C. Lp(a) quantification and apo(a) phenotyping were performed as recently described in detail (23). The serum albumin (brom-cresol green method) was measured with a kit from Roche (Basel, Switzerland). Measurements were made of microtiter plates, as previously described (25). CRP was measured on a Behring BNA nephelometer with reagents purchased from Behring Diagnostics (N Latex CRP Mono; Behring Diagnostics, Marburg, Germany). The lower detection limit of this test was 0.02 mg/dl.

Statistical Methods:

The statistical analysis was carried out with the Statistical Package for the social Sciences (SPSS) for Windows 10.0. Univariate comparisons of continuous variables between controls and the renal patients were performed by the unpaired t test or by the non-parametric Wilcoxon rank sum test in case of non-normally distributed variables. Dichotomized variables were compared using Pearson's $\chi^2$ test. ANOVA was used to compare continuous variables. between controls and renal patients sub-grouped by the three tertiles of GFR. Non-normally distributed variables were logarithmically transformed before inclusion into the analysis. The Spearman correlation test was used to correlate apoA-IV with other continuous variables. Adjustment of apoA-IV serum concentrations for age and proteinuria in patients was performed by linear regression analysis. Multiple regression analysis was used to investigate the associations of different variables with apoA-IV serum concentrations. Logistic regression analysis was performed to identify predictors for prevailing atherosclerotic events which had occurred in the past.

Results

Influence of Renal Function on apoA-IV Concentrations:

Renal patients had significantly higher total cholesterol, triglyceride and Lp(a) concentrations, yet unchanged HDL and LDL cholesterol levels as compared with controls (Table 2). The concentrations of apoA-I and apoB were significantly lower in patients. One of the most pronounced changes was in the apoA-IV concentrations which in patients were higher by nearly 70% than in controls (24.6±8.6 vs. 14.6±4.2 mg/dl, P<0.001).

TABLE 2

Serum concentrations of lipids, lipoproteins and apolipoproteins in controls and patients with renal disease[a]

|  | Controls (n = 227) | Patients with Renal Disease (n = 227) |
|---|---|---|
| Total cholesterol, mg/dl | 206 ± 41 | 215 ± 45[b] |
| HDL cholesterol, mg/dl | 43.6 ± 11.5 | 43.7 ± 14.2 |

TABLE 2-continued

Serum concentrations of lipids, lipoproteins and apolipoproteins in controls and patients with renal disease[a]

|  | Controls (n = 227) | Patients with Renal Disease (n = 227) |
|---|---|---|
| LDL cholesterol, mg/dl | 134 ± 37 | 136 ± 40 |
| Triglycerides, mg/dl; mean ± SD | 141 ± 96 | 173 ± 101[c] |
| [25th percentile, median, 75th percentile] | [84, 114, 170] | [101, 144, 223] |
| Apolipoprotein A-I, mg/dl | 157 ± 22 | 120 ± 21[c] |
| Apolipoprotein A-IV, mg/dl | 14.6 ± 4.2 | 24.6 ± 8.6[c] |
| Apolipoprotein B, mg/dl | 123 ± 30 | 107 ± 27[c] |
| Lipoprotein(a), mg/dl; mean ± SD | 20.7 ± 32.8 | 29.5 ± 32.0 |
| [25th percentile, median, 75th percentile] | [2.2, 6.9 19.4] | [4.9, 17.9, 42.5] |

[a]Data are mean ± SD and, where appropriate, [25th percentile, median, 75th percentile].
[b]P < 0.05 for comparison with control subjects.
[c]P < 0.001 for comparison with control subjects.

Figure 1:
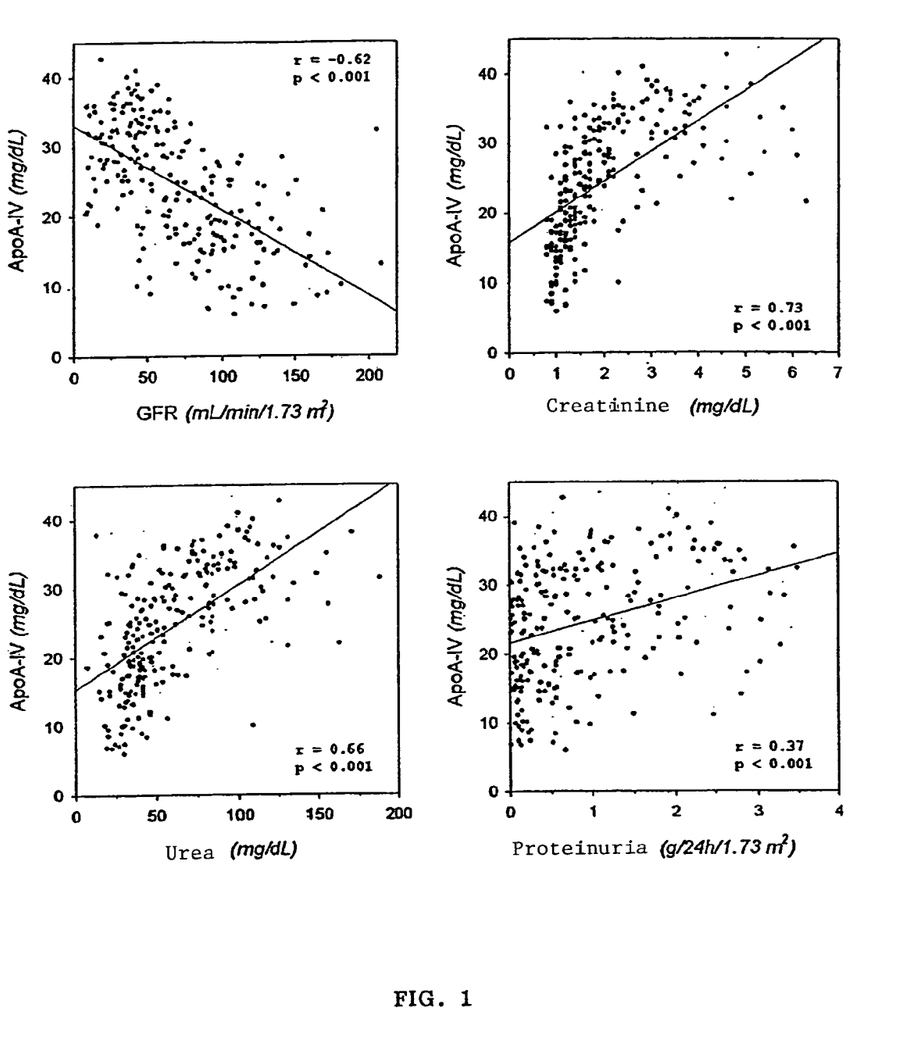
FIG. 1 shows the correlation of apoA-IV with renal function parameters (serum creatinine, serum urea, glomerulofiltration rate (GFR) and daily proteinuria, r=0.37).

The calculations of the correlation coefficients between apoA-IV and several variables in patients yielded the highest correlations with parameters of the renal function, higher concentrations of apoA-IV occurring with decreasing renal function (serum creatinine r=0.73, serum urea r=0.66, and GFR r=−0.62, daily proteinuria r=0.37) (Table 3 and FIG. 1). The correlations with age (r=0.20), total cholesterol (r=0.13), apoA-I (r=0.14) and Lp(a) (r=0.14) were much weaker. After adjustment of the apoA-IV concentrations for age and proteinuria, the correlations with renal function were still found to be significant, but no correlations with variables of lipoprotein metabolism could be found.

TABLE 3

Correlations of the serum concentrations of apolipoprotein A-IV with selected variables

| Variable | ApoA-IV Crude Values | ApoA-IV adjusted for age and proteinuria |
|---|---|---|
| Age | 0.20[b] | — |
| Body mass index | 0.00 | −0.06 |
| Creatinine | 0.73[c] | 0.56[c] |
| Urea | 0.66[c] | 0.56[c] |
| GFR | −0.62[c] | −0.54[c] |
| Proteinuria | 0.37[c] | — |
| Serum albumin | −0.09 | 0.05 |
| CRP | −0.05 | −0.16[a] |
| Total cholesterol | 0.13[a] | 0.10 |
| HDL cholesterol | 0.03 | 0.02 |
| LDL cholesterol | 0.13 | 0.11 |
| Triglycerides | 0.05 | −0.02 |
| Apolipoprotein A-I | 0.14[a] | 0.12 |
| Apolipoprotein B | 0.04 | 0.01 |
| Lipoprotein (a) | 0.14[a] | 0.07 |

[a]p < 0.05;
[b]p < 0.01;
[c]p < 0.001

The apoA-IV concentrations were calculated in three strata of renal function to investigate at which phase of the renal impairment apoA-IV concentrations start to increase (Table 4). For this, the renal patients were grouped according to the tertiles of the GFR, i.e. >90 ml/min/1.73 m², 45-90 ml/min/1.73 m², and <45 ml/min/1.73 m². ApoA-IV concentrations increased significantly with decreasing renal function (P<0.001 by ANOVA) and apoA-IV was already increased in the group of patients with primary renal disease, yet but compared to the controls their GRF values were still almost normal (>90 ml/min/1.73 m$^2$) (17.7±6.2 vs. 14.6±4.2 mg/dl, P<0.001). These findings did not change when the apoA-IV concentrations of the patients were adjusted for age and proteinuria. It was also determined whether the primary cause of renal disease influences the apoA-IV concentrations. Patients with polycystic kidney disease showed a trend to slightly higher apoA-IV concentrations when compared with those with glomerulonephritis (25.6±8.8 vs. 23.0±8.1 mg/dl, P=0.11). However, when the apoA-IV concentrations were adjusted for differences in GFR and proteinuria, these two patient groups did no longer differ by apoA-IV levels (24.5±6.7 vs. 23.5±7.1 mg/dl, P=0.48).

TABLE 4

Mean ± SD apoA-IV serum concentrations
in controls and patients with renal disease

|  | ApoA-IV, mg/dl Crude Values | ApoA-IV, mg/dl, Adjusted for Age and Proteinuria |
|---|---|---|
| Controls (n = 227) | 14.6 ± 4.2 | — |
| GFR > 90 ml/min/1.73 m$^2$ (n = 72) | 17.7 ± 6.2 | 18.4 ± 6.1 |
| GFR 45-90 ml/min/1.73 m$^2$ (n = 76) | 25.1 ± 7.9 | 24.7 ± 7.3 |
| GFR < 45 ml/min/1.73 m$^2$ (n = 79) | 30.5 ± 6.2 | 30.1 ± 6.2 |
| P value from ANOVA | <0.001$^a$ | <0.001$^a$ |

$^a$Post hoc comparisons between all possible group pairs showed P values < 0.001 (after correction according to the method of Bonferroni).

In a next step, it was analyzed by means of multiple regression analysis which variables are significantly associated with apoA-IV concentrations in renal patients. Because GFR, serum creatinine, and serum urea are strongly correlated, three different models were calculated that yielded very similar results. ApoA-IV showed the strongest associations with the parameters of renal function (GFR or serum creatinine or serum urea), which explained approximately 35% of the apoA-IV concentrations. Further, but much smaller, contributions to the apoA-IV concentrations came from proteinuria and apoA-I (Table 5).

TABLE 5

Association of variables with apoA-IV serum concentrations
in patients with mild and moderate renal failure,
determined by multiple regression analysis.

| Variable | Coefficient | SE | P | Change in R$^2$ |
|---|---|---|---|---|
| Model 1 (GRF) | | | | |
| GFR | −0.114 | 0.011 | <0.001 | 0.354 |
| ln proteinuria | 1.265 | 0.334 | <0.001 | 0.044 |
| Apolipoprotein A-I | 0.050 | 0.020 | 0.012 | 0.017 |
| Model 2 (creatinine) | | | | |
| Creatinine | 4.167 | 0.391 | <0.001 | 0.350 |
| ln proteinuria | 1.207 | 0.333 | <0.001 | 0.043 |
| Apolipoprotein A-I | 0.063 | 0.020 | 0.002 | 0.027 |
| Model 3 (urea) | | | | |
| Urea | 0.143 | 0.013 | <0.001 | 0.362 |
| ln proteinuria | 1.151 | 0.334 | 0.001 | 0.038 |
| Apolipoprotein A-I | 0.058 | 0.020 | 0.003 | 0.023 |

Variables and interaction terms that did not significantly contribute to the multiple regression model: total cholesterol, HDL and LDL cholesterol, triglycerides, apolipoprotein B, lipoprotein (a), serum albumin, smoking, body mass index, age, gender, and the interaction terms GFR*proteinuria, creatinine*proteinuria and urea*proteinuria.

"ln proteinuria" means that the variable is logarithmically transformed.

Coefficients and SE for GFR, creatinine and urea are provided on a natural scale for better interpretation. The use of logarithmically transformed values resuited in similar contributions of these variables to the models.

ApoA-IV and Atherosclerotic Complications:

Finally, an association between apoA-IV concentrations and atherosclerotic complications present was analyzed. 26 patients had experienced 36 atherosclerotic events, including 17 coronary events (mostly myocardial infarctions and aortocoronary bypasses), 9 strokes, and 10 events that affected the peripheral arterial system. Patients with atherosclerotic complications showed at least a trend to lower apoA-IV concentrations in all three ranges of GFR when compared with the patients without complications (Table 6). Most likely, because of the small size of the samples in each individual range, the difference was significant not in every group. In the analysis, also a logistic regression analysis was also performed for the entire patient group, including GRF. The most parsimonious model identified three variables associated with atherosclerotic complications: age, apoA-IV, and gender (Table 7). Each 1 mg/dl increase of apoA-IV decreased the odds ratio for an atherosclerotic complication by 8% (P=0.011). The LMW apo(a) phenotype and GFR showed a borderline association with atherosclerotic complications (Table 7).

TABLE 6

Mean (±SD) serum concentrations of apoA-IV in patients
with and without atherosclerotic events for the
three ranges of the glomerular filtration rate (GFR)

|  | Without events (n = 201) | With events (n = 26) | P |
|---|---|---|---|
| GFR > 90 ml/min/1.73 m$^2$ (n = 72) | 18.0 ± 6.3 (n = 67) | 14.0 ± 4.0 (n = 5) | 0.17 |
| GFR 45-90 ml/min/1.73 m$^2$ (n = 76) | 25.6 ± 8.1 (n = 66) | 21.4 ± 5.5 (n = 10) | 0.12 |
| GFR < 45 ml/min/1.73 m$^2$ (n = 79) | 31.1 ± 5.8 (n = 68) | 27.0 ± 7.5 (n = 11) | 0.04 |
| All patients | 24.9 ± 8.7 (n = 201) | 22.3 ± 7.7 (n = 26) | 0.15 |

TABLE 7

Logistic regression analysis investigating the
predictive value of apoA-IV and other variables for
atherosclerotic events

| Variable | Coefficient | SEM | χ$^2$ | Odds Ratio (95% CI) | P (Increase) |
|---|---|---|---|---|---|
| Age | 0.080 | 0.027 | 9.1 | 1.08 (1.03-1.14) | 0.003 |
| ApoA-IV | −0.085 | 0.033 | 6.5 | 0.92 (0.86-0.98) | 0.011 |
| Gender | 1.434 | 0.655 | 4.8 | 4.20 (1.16-15.15) | 0.028 |

Variables not in the model: LMW apo(a) phenotype (P=0.11) and ln-transformed GFR (P=0.16)

Discussion

Influence of Renal Function on apoA-IV Concentrations:

The study presented here demonstrates a strong influence of renal function on apoA-IV serum concentrations. Earlier studies had revealed that patients with end-stage renal disease have a pronounced increase of apoA-IV concentrations (18-

20, 22). However, it has been completely unknown that even a slight impairment by a renal disease with nearly normal GFR values is accompanied by a significant increase in apoA-IV concentrations. It therefore seems that apoA-IV is an early marker of renal impairment. This might also be the reason why a most recent study by Sun et al. in middleaged and elderly men and women identified diabetes mellitus as a major determinant of apoA-IV concentrations (29). Since many patients suffering from diabetes mellitus have an impaired renal function, and since already a very minor impairment of the renal function is associated with an apoA-IV increase, it is assumed that the renal function rather than diabetes mellitus per se is responsible for the apoA-IV increase. This is further supported by the present data, since diabetes mellitus was an exclusion criterion in the present study, while nevertheless an apoA-IV increase occurred. Moreover, no differences in the apoA-IV levels were observed in an earlier study in patients with end stage kidney diseases, when 189 patients with diabetes mellitus were compared with 513 non-diabetic patients (22). Other studies in patients with diabetes mellitus however, reported an elevation of apoA-IV in these patients but failed to carefully assess renal function (30, 31). Verges et al. only excluded patients with renal failure, but they did not provide detailed information about the exclusion criteria (30, 31). However, approximately 40% of the patients had microalbuminuria (31), pointing to at least a renal involvement expected to significantly affect apoA-IV concentrations.

Besides diabetes mellitus, the study by Sun and colleagues also reported a significant correlation between age and apoA-IV concentrations (29) which can mainly be explained by the renal function. It is well known that aging is associated with an enormous loss of nephrons and the glomerular filtration rate. A person at the age of 70 years has a GFR of only about 60-70% of that of a young adult. Therefore, in many instances the GFR is already in a range as in the mean GFR tertile of our patients who already exhibited a marked increase of apoA-IV levels. When apoA-IV in the control group recruited by the PROCAM study was correlated with age, no significant correlation was observed (r=0.057, P=0.39). This can simply be explained by the fact that a large number of controls with renal impairment was excluded from the analysis by taking a serum creatinine of >1.5 mg/dl and/or macroalbuminuria as exclusion criteria. This clearly indicates the need of thoroughly controlling of the apoA-IV concentrations for renal function in case control studies. If renal function is not considered, the interpretation of results can be misleading when differences in renal function exist between test persons and controls. The consequence could be either falsely positive or falsely negative associations, depending on the distribution of renal function in test persons and controls. The question remains to be answered whether apoA-IV in renal problems is fully functional. It could be assumed that uremia has an influence e.g. on the enzyme-activating and anti-oxidant properties of apoA-IV. An increase in apoA-IV to compensate the dysfunction is, however, not probable. It seems much more probable that the apoA-IV increase is secondary, caused by a catabolic blockage in the kidney, which is supported by observations in rats that apoA-IV is catabolized by kidney and liver. The histological analysis showed that apoA-IV is localized within proximal tubular cells and in tubular lumen (32). Because of its molecular weight of approximately 46 kDa, apoA-IV can be filtered by glomeruli at least in its non-lipoprotein-bound (free) form. The uptake by proximal tubular cells could then be followed by decomposition. However, it still has to be determined whether the catabolic pathway in humans is the same as in rats.

ApoA-IV and Atherosclerotic Complications:

Recently, significantly lower apoA-IV levels were reported for the first time in 114 male white test persons with angiographically defined CAD compared with 114 age-adjusted male controls (10.2±3.8 mg/dl vs. 15.1±4.0 mg/dl, P<0.001). This inverse relationship between apoA-IV levels and the presence of CAD was confirmed in an independent sample of 68 Asian Indian men with angiographically documented CAD and 68 age-matched controls. In line with this finding, lower apoA-IV concentrations were observed in patients who had already experienced an atherosclerotic event when compared with controls without an event. This was observed in all three ranges of GFR, yet only in the range with the poorest GFR, the conventional significance level was reached, which might be explained by the small number of patients with events in one individual range (Table 6). When the whole group was considered in the logistic regression analysis, with GFR being presented to the statistical model, apoA-IV, irrespective of GFR, proved to be a reliable predictor for events (Table 7). The evidence making this connection highly probable is strong: cell culture studies showing a participation of apoA-IV in several steps of reverse cholesterol transport (9-14) as well as antioxidant properties (33); overexpression of human and mouse apoA-IV in mice led to a decrease in atherosclerosis (16, 17); and finally, first results of lower apoA-IV concentrations in males with angiographically proven CAD (34).

The results of this and another study (34) are in contrast to an investigation in patients with noninsulin-dependent diabetes mellitus that described significantly higher apoA-IV concentrations in patients in comparison with those without macrovascular complications (31). The explanation for this discrepancy might be the increased prevalence of microalbuminuria and the concomitant renal impairment in patients with diabetes with macrovascular complications. Therefore, higher apoA-IV levels in patients with diabetes with macrovascular complications may simply reflect their impaired renal function.

At the moment, too little is known about the regulation of apoA-IV serum concentrations which could be used for the development of a therapeutic intervention. As soon as therapeutic agents that increase the apoA-IV concentration have been developed, they will be used as one of the most convincing experiments for investigating the pathogenicity of apoA-IV.

One might ask why patients with renal disease have such a high risk for atherosclerotic complications (35) when they have such high apoA-IV concentrations. If apoA-IV has indeed antiatherogenic properties, these patients should be more protected than nonrenal patients. This argument is quite intriguing from a univariate point of view. However, it should be kept in mind that in these patients, several atherosclerosis risk factors are substantially shifted towards an unfavorable profile (35). Besides the changes in traditional atherosclerosis risk factors, marked changes for Lp(a) and homocysteine have recently been shown (for reviews, see (36, 37)), even at stages when renal disease involves only slight changes in the GFR (23, 38, 39). Several studies demonstrated that homocysteine as well as Lp(a) and especially Lp(a) of LMW apo(a) phenotypes are important risk factors for atherosclerosis in these patients (40-48). Whether apoA-IV counteracts this burden has not yet been determined, yet this assumption is supported by the lower apoA-IV levels in those with atherosclerotic problems.

It is an interesting finding that the present patients had normal HDL cholesterol values but markedly decreased apoA-I levels. Other studies usually investigated patients with renal impairment in more advanced stages with lower GFR concentrations and described decreased HDL cholesterol concentrations (49-51). In contrast to these investigations, the present patients had a higher mean GFR of approximately 70 ml/min/1.73 $m^2$, suggesting that the decrease in HDL cholesterol is preceded by an apoA-I depletion or a lipid particle accumulation of HDL cholesterol which could be a sign of an impaired reverse cholesterol transport pathway. Because apoA-I and apoA-IV show substantial functional overlap (e.g. LCAT activation), it remains to be determined whether an increase of apoA-IV is an attempt to compensate the decrease of the apoA-I.

In summary, the present data clearly show that apoA-IV starts to increase during the earliest phases of renal insufficiency, which makes apoA-IV an early marker of renal impairment. Moreover, apoA-IV seems to be associated with atherosclerotic complications in patients with mild to moderate renal failure.

REFERENCES

1. Utermann G, Beisiegel U: Apolipoprotein A-IV: a protein occurring in human mesenteric lymph chylomicrons and free in plasma. Isolation and quantification. *Eur J Biochem* 99:333-343, 1979.
2. Green P H R, Glickman R M, Riley J W, Qinet E: Human apolipoprotein A-IV. Intestinal origin and distribution in plasma. *J Clin Invest* 65:911-919, 1980.
3. Duverger N, Ghalim N, Ailhaud G, Steinmetz A, Fruchart J-C, Castro G: Characterisation of apoA-IV-containing lipoprotein particles isolated from human plasma and interstitial fluid. *Arterioscler Thromb* 13:126-132, 1993.
4. Von Eckardstein A, Huang Y, Wu S, Sarmadi A S, Schwarz S, Steinmetz A, Assmann G: Lipoproteins containing apolipoprotein A-IV but not apolipoprotein A-I take up and esterify cell-derived cholesterol in plasma. *Arterioscler Thromb Vasc Biol* 15:1755-1763, 1995.
5. Apfelbaum T F, Davidson N O, Glickman R M: Apolipoprotein A-IV synthesis in rat intestine: regulation by dietary triglyceride. *Am J Physiol* 252:G662-G666 1987.
6. Fujimoto K, Cardelli J A, Tso P: Increased apolipoprotein A-IV in rat mesenteric lymph after lipid meal acts as a physiological signal for satiation. *Am J Physiol* 262: G1002-G1006 1992.
7. Aalto-Setälä K, Bisgaier C L, Ho A, Kieft K A, Traber M G, Kayden H J, Ramakrishnan R, Walsh A, Essenburg A D, Breslow J L: Intestinal expression of human apolipoprotein A-IV in transgenic mice fails to influence dietary lipid absorption or feeding behavior. *J Clin Invest* 93:1776-1786, 1994.
8. Weinstock P H, Bisgaier C L, Hayek T, Aalto-Setala K, Sehayek E, Wu L, Sheiffele P, Merkel M, Essenburg A D, Breslow J L: Decreased HDL cholesterol levels but normal lipid absorption, growth, and feeding behavior in apolipoprotein A-IV knockout mice. *J Lipid Res* 38:1782-1794, 1997.
9. Stein O, Stein Y, Lefevre M, Roheim P S: The role of apolipoprotein A-IV in reverse cholesterol transport studied with cultured cells and liposomes derived from another analog of phosphatidylcholine. *Biochim Biophys Acta* 878: 7-13, 1986.
10. Dvorin E, Gorder N L, Benson D M, Gotto Jr. A M: Apolipoprotein A-IV. A determinant for binding and uptake of high density lipoproteins by rat hepatocytes. *J Biol Chem* 261:15714-15718, 1986.
11. Steinmetz A, Barbaras R, Ghalim N, Clavey V, Fruchart J-C, Ailhaud G: Human apolipoprotein A-IV binds to apolipoprotein A-I/A-II receptor sites and promotes cholesterol efflux from adipose cells. *J Biol Chem* 265:7859-7863, 1990.
12. Steinmetz A, Utermann G: Activation of lecithin:cholesterol acyltransferase by human apolipoprotein A-IV. *J Biol Chem* 260:2258-2264, 1985.
13. Chen C H, Albers J J: Activation of lecithin:cholesterol acyltransferase by apolipoproteins E-2, E-3 and A-IV isolated from human plasma. *Biochim Biophys Acta* 836:279-285, 1985.
14. Goldberg I J, Scheraldi C A, Yacoub L K, Saxena U, Bisgaier C L: Lipoprotein ApoC-II. activation of lipoprotein lipase. Modulation by apolipoprotein A-IV. *J Biol Chem* 265:4266-4272, 1990.
15. Guyard-Dangremont V, Lagrost L, Gambert P: Comparative effects of purified apolipoproteins A-I, A-II, and A-IV on cholesteryl ester transfer protein activity. *J Lipid Res* 35:982-992, 1994.
16. Duverger N, Tremp G, Caillaud J M, Emmanuel F, Castro G, Fruchart J C, Steinmetz A, Denèfle P: Protection against atherogenesis in mice mediated by human apolipoprotein A-IV. *Science* 273:966-968, 1996.
17. Cohen R D, Castellani L W, Qiao J H, Van Lenten B J, Lusis A J, Reue K: Reduced aortic lesions and elevated high density lipoprotein levels in transgenic mice overexpressing mouse apolipoprotein A-IV. *J Clin Invest* 99:1906-1916, 1997.
18. Nestel P J, Fide N H, Tan M H: Increased lipoproteinremnant formation in chronic renal failure. *N Engl J Med* 307:329-333, 1982.
19. Seishima M, Muto Y: An increased apo A-IV serum concentration of patients with chronic renal failure on hemodialysis. *Clin Chim Acta* 167:303-311, 1987.
20. Dieplinger H, Lobentanz E-M, König P, Graf H, Sandholzer C, Matthys E, Rosseneu M, Utermann G: Plasma apolipoprotein A-IV metabolism in patients with chronic renal disease. *Eur J Clin Invest* 22:166-174, 1992.
21. Dieplinger H, Schoenfeld P Y, Fielding J: Plasma cholesterol metabolism in end-stage renal disease: difference between treatment by hemodialysis or peritoneal dialysis. *J Clin Invest* 77:1071-1083, 1986.
22. Kronenberg F, König P, Neyer U, Auinger M, Pribasnig A, Lang U, Reitinger J, Pinter G, Utermann G, Dieplinger H: Multicentre study of lipoprotein(a) and apolipoprotein(a) phenotypes in patients with end-stage renal disease treated by hemodialysis or continuous ambulatory peritoneal dialysis. *J Am Soc Nephrol* 6:110-120, 1995.
23. Kronenberg F, Kuen E, Ritz E, Junker R, König P, Kraatz G, Lhotta K, Mann JFE, Müller G A, Neyer U, Riegel W, Riegler P, Schwenger V, Von Eckardstein A: Lipoprotein(a) serum concentrations and apolipoprotein
(a) phenotypes in mild and moderate renal failure. *J Am Soc Nephrol* 11:105-115, 2000.
24. Assmann G, Schulte H, Von Eckardstein A: Hypertriglyceridemia and elevated lipoprotein(a) are risk factors for major coronary events in middle-aged men. *Am J Cardiol* 77:1179-1184, 1996.
25. Kronenberg F, Lobentanz E-M, König P, Utermann G, Dieplinger H: Effect of sample storage on the measurement of lipoprotein(a), apolipoproteins B and A-IV, total and high-density lipoprotein cholesterol and triglycerides. *J Lipid Res* 35:1318-1328, 1994.
26. Gaspari F, Perico N, Matalone M, Signorini O, Azzollini N, Mister M, Remuzzi G: Precision of plasma clearance of iohexol for estimation of GFR in patients with renal disease. *J Am Soc Nephrol* 9:310-313, 1998.

27. Cockcroft D W, Gault M H: Prediction of creatinine clearance from serum creatinine. *Nephron* 16:31-41, 1976.
28. Rosseneu M, Michiels G, Dekeersgieter W, Bury J B, De Slypere J P, Dieplinger H, Utermann G: Human apolipoprotein A-IV quantitation by sandwich enzyme linked immunosorbent assay. *Clin Chem* 34:739-743, 1988.
29. Sun Z, Larson I A, Ordovas J M, Barnard J R, Schaefer E J: Effects of age, gender, and lifestyle factors on plasma apolipoprotein A-IV concentrations. *Atherosclerosis* 151: 381-388, 2000.
30. Verges B L, Vaillant G, Goux A, Lagrost L, Brun J M, Gambert P: Apolipoprotein A-IV levels and phenotype distribution in NIDDM. *Diabetes Care* 17:810-817, 1994.
31. Verges B L, Lagrost L, Vaillant G, Petit J M, Cohen M, Gambert P, Brun J M: Macrovascular disease is associated with increased plasma apolipoprotein A-IV levels in NIDDM. *Diabetes* 46:125-132, 1997.
32. Dallinga-Thie G M, Van't Hooft F M, van Tol A: Tissue sites of degradation of high density lipoprotein apolipoprotein A-IV in rats. *Arteriosclerosis* 6:277-284, 1986.
33. Qin X F, Swertfeger D K, Zheng S Q, Hui D Y, Tso P: Apolipoprotein AIV: A potent endogenous inhibitor of lipid oxidation. *Am J Physiol* 274: H1836-H18401998.
34. Kronenberg F, Stühlinger M, Trenkwalder E, Geethanjali F S, Pachinger O, Von Eckardstein A, Dieplinger H: Low apolipoprotein A-IV plasma concentrations in men with coronary artery disease. *J Am Coll Cardiol* 36:751-757, 2000.
35. London G M, Drüeke T B: Atherosclerosis and arteriosclerosis in chronic renal failure. *Kidney Int* 51:1678-1695, 1997.
36. Bostom A G, Lathrop L: Hyperhomocysteinemia in end-stage renal disease: Prevalence, etiology, and potential relationship to arteriosclerotic outcomes. *Kidney Int* 52:10-20, 1997.
37. Kronenberg F: Homocysteine, lipoprotein(a) and fibrinogen: metabolic risk factors for cardiovascular complications of chronic renal disease. *Curr Opin Nephrol Hypertens* 7:271-278, 1998.
38. Bostom A G, Kronenberg F, Jacques P F, Kuen E, Ritz E, König P, Kraatz G, Lhotta K, Mann J F E, Müller G A, Neyer U, Riegel W, Schwenger V, Riegler P, Selhub J: Proteinuria and plasma total homocysteine levels in chronic renal disease patients with a normal range serum creatinine: critical impact of true glomerular filtration rate. *Athero sclerosis* (in press).
39. Bostom A G, Kronenberg F, Gohh R Y, Schwenger V, Kuen E, König P, Kraatz G, Lhotta K, Mann J F E, Müller G A, Neyer U, Riegel W, Riegler P, Ritz E, Selhub J: Chronic renal transplantation: a model for the hyperhomocysteinemia of renal insufficiency. *Atherosclerosis* 156: 227-230, 2001.
40. Jungers P, Massy Z A, Khoa T N, Fumeron C, Labrunie N, Lacour B, Descamps-Latscha B, Man N K: Incidence and risk factors of atherosclerotic cardiovascular accidents in predialysis chronic renal failure patients: a prospective study. *Nephrol Dial Transplant* 12:2597-2602, 1997.
41. Bachmann J, Tepel M, Raidt H, Riezler R, Graefe U, Langer K, Zidek W: Hyperhomocysteinemia and the risk for vascular disease in hemodialysis patients. *J Am Soc Nephrol* 6:121-125, 1995.
42. Robinson K, Gupta A, Dennis V, Arheart K, Chaudhary D, Green R, Vigo P, Mayer E L, Selhub J, Kutner M, Jacobsen D W: Hyperhomocysteinemia confers an independent increased risk of atherosclerosis in end-stage renal disease and is closely linked to plasma folate and pyridoxine concentrations. *Circulation* 94:2743-2748, 1996.
43. Bostom A G, Shemin D, Verhoef P, Nadeau M R, Jacques P F, Selhub J, Dworkin L, Rosenberg I H: Elevated fasting total plasma homocysteine levels and cardiovascular disease outcomes in maintenance dialysis patients. A prospective study. *Arterioscler Thromb Vasc Biol* 17:2554-2558, 1997.
44. Moustapha A, Naso A, Nahlawi M, Gupta A, Arheart K L, Jacobsen D W, Robinson K, Dennis V W: Prospective study of hyperhomocysteinemia as an adverse cardiovascular risk factor in end-stage renal disease. *Circulation* 97:138-141, 1998.
45. Cressman M D, Heyka R J, Paganini E P, O'Neil J, Skibinski C I, Hoff H F: Lipoprotein(a) is an independent risk factor for cardiovascular disease in hemodialysis patients. *Circulation* 86:475-482, 1992.
46. Kronenberg F, Kathrein H, König P, Neyer U, Sturm W, Lhotta K, Gröchenig E, Utermann G, Dieplinger H: Apolipoprotein(a) phenotypes predict the risk for carotid atherosclerosis in patients with end-stage renal disease. *Arterioscler Thromb* 14:1405-1411, 1994.
47. Koch M, Kutkuhn B, Trenkwalder E, Bach D, Grabensee B, Dieplinger H, Kronenberg F:. Apolipoprotein B, fibrinogen, HDL cholesterol and apolipoprotein(a) phenotypes predict coronary artery disease in hemodialysis patients. *J Am Soc Nephrol* 8:1889-1898, 1997.
48. Kronenberg F, Neyer U, Lhotta K, Trenkwalder E, Auinger M, Pribasnig A, Meisl T, König P, Dieplinger H: The low molecular weight apo(a) phenotype is an independent predictor for coronary artery disease in hemodialysis patients: a prospective follow-up. *J Am Soc Nephrol* 10:1027-1036, 1999.
49. Attman P-O, Alaupovic P: Lipid and apolipoprotein profiles of uremic dyslipoproteinemia. Relation to renal function and dialysis. *Nephron* 57:401-410, 1991.
50. Attman P O, Alaupovic P, Gustafson A: Serum apolipoprotein profile of patients with chronic renal failure. *Kidney Int* 32:368-375, 1987.
51. Attman P O, Alaupovic P, Tavella M, Knight-Gibson C: Abnormal lipid and apolipoprotein composition of major lipoprotein density classes in patients with chronic renal failure. *Nephrol Dial Transplant* 11:63-69, 1996.

The invention claimed is:

1. A method of diagnosing early stage renal impairment in a human having a glomerular filtration rate (GFR) of more than 90 ml/min/1.73 m$^2$, comprising:
    measuring an amount of apoA-IV in a plasma sample or a serum sample of the human;
    comparing the measured amount of apoA-IV with a reference value obtained from a human without renal impairment; and
    diagnosing early stage renal impairment based on the comparison of the measured amount of apoA-IV with the reference value, wherein early stage renal impairment is defined by a glomerular filtration rate (GFR) of more than 90 ml/min/1.73 m$^2$, and wherein an early stage of a renal impairment in the human is diagnosed by way of an increased level of apoA-IV in the plasma sample or the serum sample as compared to the reference value obtained from a human without renal impairment.

2. The method of claim 1, wherein the increased level is higher by at least 20% than the reference value obtained from a human without renal impairment.

3. The method of claim 1, wherein the increased level is higher by at least 50% than the reference value obtained from a human without renal impairment.

4. The method of claim 1, wherein the increased level is higher by at least 70% than the reference value obtained from a human without renal impairment.

5. The method of claim 1, wherein the reference value is between 10 and 18 mg of apoA-IV/dl of serum.

6. The method of claim 1, wherein the early stage renal impairment is early stage glomerulonephritis, early stage polycystic kidney disease, early stage chronic pyelonephritis, or early stage diabetic nephropathy.

7. The method of claim 1, wherein for humans with coronary artery diseases or for humans with atherosclerotic complications, the reference value is obtained from a human without a renal impairment but with a coronary artery disease or an atherosclerotic complication.

8. The method of claim 7, wherein the reference value obtained from a human without a renal impairment but with a coronary artery disease or an atherosclerotic complication is lower by at least 20% than the reference value for humans without renal impairment and without coronary artery diseases or atherosclerotic complications.

9. The method of claim 7, wherein the reference value obtained from a human without a renal impairment but with a coronary artery disease or an atherosclerotic complication is lower by at least 40% than the reference value for humans without renal impairment and without coronary artery diseases or atherosclerotic complications.

10. The method of claim 7, wherein the reference value obtained from a human without a renal impairment but with a coronary artery disease or an atherosclerotic complication is lower by at least 60% than the reference value for humans without renal impairment and without coronary artery diseases or atherosclerotic complications.

11. The method of claim 7, wherein the reference value is between 6 and 14 mg of apoA-IV/dl of serum.

12. The method claim 11, wherein an early stage renal impairment of a human with a coronary artery disease or with atherosclerotic complications is diagnosed by way of a level of higher than 14 mg of apoA-IV/dl of serum.

13. The method claim 11, wherein an early stage renal impairment of a human with a coronary artery disease or with atherosclerotic complications is diagnosed by way of a level of higher than 18 mg of apoA-IV/di of serum.

14. The method claim 11, wherein an early stage renal impairment of a human with a coronary artery disease or with atherosclerotic complications is diagnosed by way of a level of higher than 22 mg of apoA-IV/dl of serum.

15. A method of diagnosing early stage renal impairment in a human having a glomerular filtration rate (GFR) of more than 90 ml/min/1.73 m$^2$, comprising:
    measuring an amount of apoA-IV in a serum sample of the human;
    comparing the measured amount of apoA-IV with a reference value, wherein the reference value is between 10 and 18 mg of apoA-IV/dl of serum; and
    diagnosing early stage renal impairment based on the comparison of the measured amount of apoA-IV with the reference value, wherein early stage renal impairment is defined by a glomerular filtration rate (GFR) of more than 90 ml/min/1.73 m$^2$, and wherein an early stage of a renal impairment in the human is diagnosed when the measured value of apoA-IV in the serum sample is higher than 18 mg of apoA-IV/dl of serum.

16. The method of claim 15, wherein an early stage of a renal impairment is diagnosed when the measured value of apoA-IV in the serum sample is higher than 22 mg of apoA-IV/dl of serum.

17. The method of claim 15, wherein an early stage of a renal impairment is diagnosed when the measured value of apoA-IV in the serum sample is higher than 28 mg of apoA-IV/dl of serum.

* * * * *

UNITED STATES PATENT AND TRADEMARK OFFICE
CERTIFICATE OF CORRECTION

PATENT NO. : 7,842,463 B2  
APPLICATION NO. : 10/485039  
DATED : November 30, 2010  
INVENTOR(S) : Florian Kronenberg Page 1 of 1

It is certified that error appears in the above-identified patent and that said Letters Patent is hereby corrected as shown below:

In claim 13, column 18, line 6, delete "apoA-IV/di" and insert --apoA-IV/dl-- therefor.

Signed and Sealed this  
Fifteenth Day of March, 2011

David J. Kappos  
*Director of the United States Patent and Trademark Office*

UNITED STATES PATENT AND TRADEMARK OFFICE
CERTIFICATE OF CORRECTION

| | | |
|---|---|---|
| PATENT NO. | : 7,842,463 B2 | Page 1 of 1 |
| APPLICATION NO. | : 10/485039 | |
| DATED | : November 30, 2010 | |
| INVENTOR(S) | : Kronenberg | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1895 days.

Signed and Sealed this
Third Day of May, 2011

David J. Kappos
*Director of the United States Patent and Trademark Office*